United States Patent [19]

Meijer

[11] Patent Number: 5,269,832

[45] Date of Patent: Dec. 14, 1993

[54] METHOD AND APPARATUS FOR CONTINUOUSLY MEASURING THE CONCENTRATION OF CHEMICALS IN SOLUTIONS

[75] Inventor: Robert S. Meijer, San Diego, Calif.

[73] Assignee: Winfield Industries, San Diego, Calif.

[21] Appl. No.: 893,233

[22] Filed: Jun. 3, 1992

[51] Int. Cl.⁵ ............................................ G01N 35/00
[52] U.S. Cl. ............................ 95/25; 55/274;
73/25.01; 95/254; 95/263; 96/203; 204/153.13;
204/431; 422/82.01; 422/82.12; 436/125
[58] Field of Search ............... 55/18, 37, 46, 68, 71,
55/196, 270, 274, 316, 20; 73/25.01; 210/94,
96.1, 188, 742, 745, 767, 746, 703, 718, 218, 219,
738; 422/62, 82.01, 82.12; 436/125, 52, 127,
147; 423/477; 204/400, 406, 407, 408, 431,
153.1, 153.13, 153.16

[56] References Cited

U.S. PATENT DOCUMENTS

| Re. 32,920 | 5/1989 | Matson et al. | 204/400 |
|---|---|---|---|
| 3,578,404 | 5/1971 | Walles et al. | 422/82.12 |
| 4,084,747 | 4/1978 | Alliger | 239/4 |
| 4,128,454 | 12/1978 | Schleinkofer | 55/18 |
| 4,270,925 | 6/1981 | Isa et al. | 436/125 |
| 4,504,442 | 3/1985 | Rosenblatt | 422/37 |
| 4,533,691 | 8/1985 | Kahalil et al. | 524/401 |
| 4,578,185 | 3/1986 | Wilson et al. | 210/85 |
| 4,671,882 | 6/1987 | Douglas et al. | 210/720 |
| 4,731,193 | 3/1988 | Mason et al. | 252/95 |
| 4,809,915 | 3/1989 | Koffsky et al. | 241/36 |
| 4,822,513 | 4/1989 | Corby | 252/106 |
| 4,861,514 | 8/1989 | Hutchings | 252/187.21 |
| 4,889,654 | 12/1989 | Mason et al. | 252/100 |
| 4,917,238 | 4/1990 | Schumacher | 206/223 |
| 4,923,677 | 5/1990 | Simon et al. | 422/37 |
| 4,925,645 | 5/1990 | Mason | 423/477 |
| 4,945,992 | 8/1990 | Sacco | 166/310 |
| 5,009,875 | 4/1991 | Kelley et al. | 423/477 |
| 5,110,580 | 5/1992 | Rosenblatt et al. | 423/477 |
| 5,165,910 | 11/1992 | Oikawa et al. | 423/477 |
| 5,190,725 | 3/1993 | Meijer et al. | 423/477 |

FOREIGN PATENT DOCUMENTS

| 959238 | 12/1974 | Canada | 23/146 |
|---|---|---|---|
| 767020 | 10/1980 | U.S.S.R. | 436/125 |

OTHER PUBLICATIONS

Block, Seymour S., *Disinfection, Sterilization, and Preservation*, pp. 540–544, Lea & Febiger, Philadelphia, 1983.
Medical SafeTEC, Series Twelve Five, article/advertisement, Indianapolis, Indiana, date unknown.
*Principles of Thermal Destruction of Microorganisms*, Mode of Action, excerpt from text, pp. 755–759, 797, date unknown.
*Interfacial Phenomena*, Mode of Action, excerpt from text, pp. 822–825, date unknown.
Whitten, Kenneth W. and Gailey, Kenneth D., *General Chemistry*, Chapter 14, Chemical Kinetics, pp. 478–490, date unknown.

*Primary Examiner*—Joseph W. Drodge
*Attorney, Agent, or Firm*—Nydegger & Associates

[57] ABSTRACT

A method and apparatus for continuously monitoring the concentration of a target chemical in a solution, such as chlorine dioxide in sewage or waste water, includes a holding tank, a bubbler chamber, and an air pump for directing air bubbles through the solution held in the bubbler chamber. Gases discharged from the solution by the air bubbles are collected in the bubbler chamber. These discharged gases include a quantity of the target chemical present in the solution as a dissolved gas. The concentration of the chemical in the discharged gases is then measured with a sensor such as a polarographic probe. This concentration along with the measured temperature of the solution is used as an analog to determine the concentration of the chemical in the solution.

26 Claims, 1 Drawing Sheet

METHOD AND APPARATUS FOR CONTINUOUSLY MEASURING THE CONCENTRATION OF CHEMICALS IN SOLUTIONS

TECHNICAL FIELD

The present invention relates generally to the chemical analysis of solutions such as waste solutions. More particularly, the present invention relates to a method and apparatus particularly, though not exclusively, adapted to the continuous measurement of particular chemical concentrations in aqueous and other waste solutions.

BACKGROUND OF THE INVENTION

Many industrial processes require periodic or continuous monitoring and measurement of the concentration of particular chemicals dissolved in a solution. As an example, prior to discharge, treated plant wastes or sewage must be tested for the presence of particular components. Such measurements can be either "continuous" or "sampling". From the standpoint of process control, continuous measurements are preferable to sampling or batch measurements.

Prior art devices for effecting such measurements include specific ion probes, optical density devices and pH meters. A variety of each of these types of probes is well known in the art.

In general, such prior art devices do not function effectively in the continuous monitoring of plant wastes and sewage. These solutions may include a wide variety of and a relatively high concentration of chemicals (other than those being monitored). For this reason, these solutions typically require a sampling system, such as sequential titration, that isolates the chemical to be quantified from other interfering chemicals before an attempt is made to determine its concentration. Even with such conventional sampling techniques, however, the make up of the waste solution may be such that accurate results are not provided.

One specific example of a chemical that is difficult to monitor in waste water treatment, is chlorine or chlorine dioxide. While clean water can be continuously monitored for chlorine or chlorine dioxide concentration, this same measurement is normally extraordinarily difficult in plant waste or sewage solutions undergoing treatment.

There is then, a need in the art for a system that effectively and continuously monitors the concentration of particular chemicals contained in various solutions such as plant waste and sewage discharges. The method and apparatus of the present invention recognizes that such solutions can be continuously monitored by analyzing the presence of a target chemical contained in the solution as a dissolved gas. One method of effecting this analysis is by directing a stream of bubbles through the waste solution to release gases from the solution which include a quantity of the target chemical. These gases are then collected and the concentration of the target chemical is determined.

Accordingly it is an object of the present invention to provide a method and apparatus for continuously monitoring the presence and concentration of particular chemicals present in solutions such as sewage or waste water solutions. It is a further object of the present invention to provide a method and apparatus for directing a stream of bubbles through a solution and for collecting and analyzing gases stripped by the bubbles to ascertain the concentration of particular chemicals in the solution. Yet another object of the present invention is to provide a method and apparatus for continuously monitoring plant or sewage waste solutions that are effective, inexpensive, and simple in operation.

SUMMARY OF THE INVENTION

In accordance with the present invention a method and apparatus for continuously monitoring the presence and concentration of particular chemicals in solutions is provided. The method of the invention, broadly stated, includes the steps of;

directing a stream of gas bubbles through a solution;

measuring a temperature of the solution;

collecting the gases discharged from the solution by gas bubbles;

measuring the concentration of a target chemical present in the collected gases; and determining the concentration of the target chemical in the solution using the measured concentration of the target chemical in the collected gases and the measured temperature of the solution as an analog.

In an illustrative embodiment of the invention, a system is adapted for measuring the concentration of chlorine dioxide in a solution of waste water, such as treated sewage or industrial discharges. Chlorine dioxide, like many other chemicals in solution, is present as a dissolved gas. When a solution of waste water and the dissolved chlorine dioxide gas within the solution are exposed to a stream of air bubbles, some of the chlorine dioxide gas in solution leaves the solution, with the stream of bubbles exiting the solution. This discharged gas stream can be collected and analyzed to ascertain the amount of chlorine dioxide present in the solution.

This analysis is possible because in general, the amount of chlorine dioxide gas released by the air stream is a function of its concentration in the solution and the temperature of the solution. The collected gas stream thus provides an analog of the relative concentration of the target chemical in the solution. A measurement of the chlorine dioxide gas within the collected gas stream can be accurately performed using a sensor such as a polarographic gas probe. Using this method, it is much easier to effect an accurate analysis of the target gas concentration because the discharged bubbles rather than a highly contaminated waste water solution provides the background for the measurement.

A system, constructed in accordance with the invention includes a holding tank which continuously receives and discharges a quantity of waste water. This waste water may be continuously stirred or agitated to achieve homogeneity.

An air or gas pump is adapted to bubble an air or nitrogen stream through a bubbler chamber having a supply of waste water. The gas discharged from the waste water, by the air stream, is collected in the bubbler chamber. The concentration of the chlorine dioxide gas within the collected air stream is then measured.

An electrochemical sensor, such as a polarographic probe, may be used to measure the concentration of the chlorine dioxide within the discharged gas stream. This measurement along with the measured temperature of the waste water provides an analog of the concentration of the chlorine dioxide gas contained within the waste water. After analysis, the collected gas stream may be scrubbed to remove noxious gases and vented to the atmosphere.

Signals from the polarographic and temperature sensors are processed by a processor such as a computer or microprocessor using preprogrammed instructions. Using these signals and instructions, the processor determines the concentration of the chlorine dioxide in the solution. This information can then be recorded or displayed, or used to effect process controls.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts.

DESCRIPTION OF PREFERRED EMBODIMENTS

Figure 1:
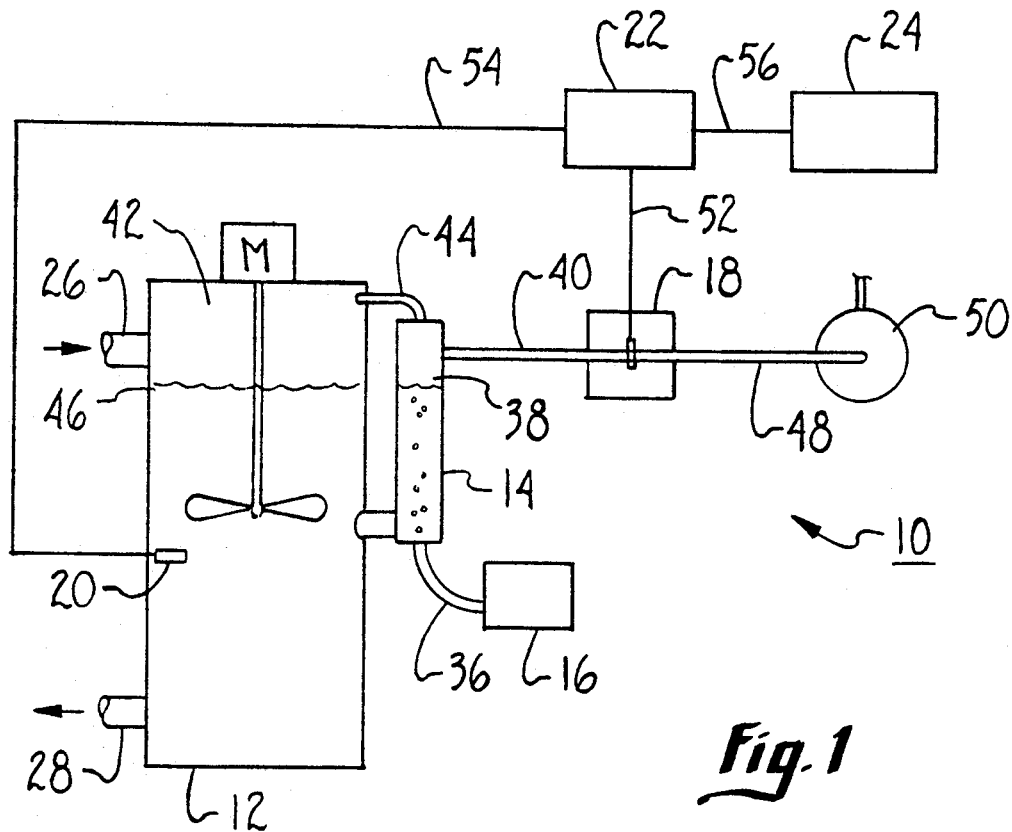
FIG. 1 is a schematic diagram of a system constructed in accordance with the invention for continuously measuring the concentration of particular chemicals contained in a solution.

Referring now to FIG. 1 a system for continuously measuring the concentration of chlorine dioxide ($ClO_2$) in a solution of waste water is shown and designated as 10. The system 10, generally stated, includes;
- a holding tank 12 for receiving waste water;
- a bubbler chamber 14 in fluid communication with the holding tank 12 for holding waste water and collecting gases discharged from the waste water;
- an air pump 16 for directing bubbles through the waste water in the bubbler chamber 14 for collection in the bubbler chamber 14;
- an electrochemical or other sensor 18 for detecting the concentration of chlorine dioxide in the gases discharged from the waste water by the bubbles;
- a temperature probe 20 for measuring the temperature of the waste water;
- a processor 22 for analyzing signals from the chemical sensor 18 and temperature probe 20 and for using preprogrammed instructions to determine the concentration of chlorine dioxide in the waste water; and
- a digital display 24 for displaying the data.

Figure 2:
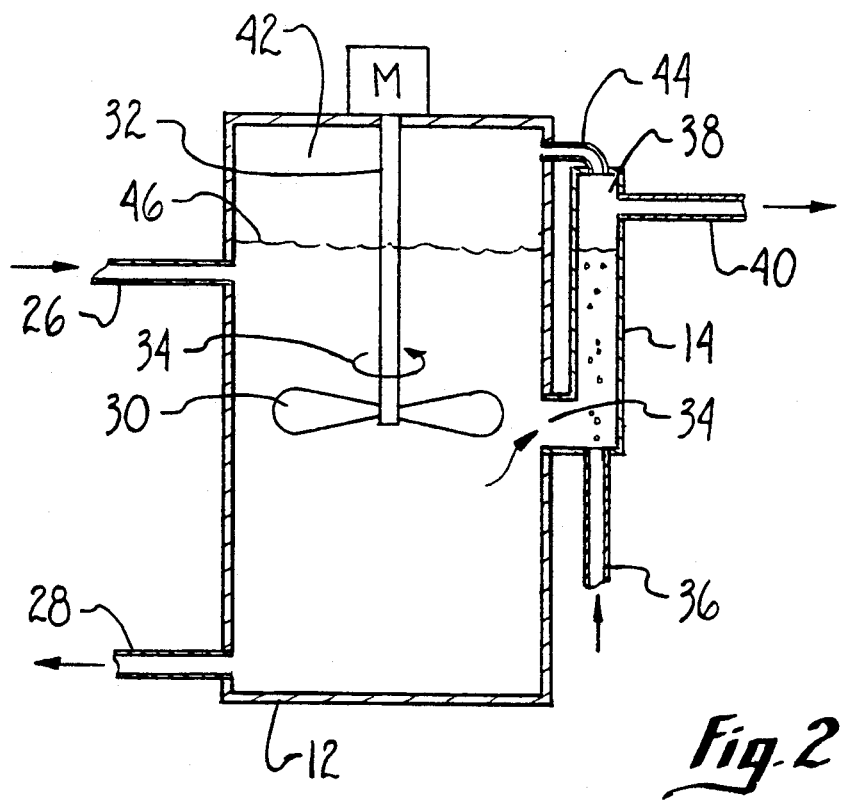
FIG. 2 is an enlarged schematic view of a portion of the system shown in FIG. 1.

With reference to FIG. 2, the holding tank 12 is adapted to hold a quantity of waste water for testing in accordance with the method of the invention. The holding tank 12 may be an open or closed vessel adapted to hold a relatively large quantity of waste water. In addition an inlet conduit 26 may be provided for continuously directing waste water into the holding tank 12 and an outlet conduit 28 may be provided for continuously discharging waste water from the holding tank 12.

A stirrer 30 is rotatably mounted to the holding tank 12 for continuously stirring the waste water to provide a homogeneous mixture. The stirrer 30 may be connected to a motor driven shaft 32 for rotation about the longitudinal axis of the shaft 32 as indicated by rotational arrow 34. The stirrer 30 also functions to direct a continuous supply of waste water into the bubbler chamber 14 as indicated by the flow arrows in FIG. 2.

The bubbler chamber 14 is in fluid communication with the holding tank 12 and is adapted to receive waste water from the holding tank 12 through an inlet 35. The bubbler chamber 14 is preferably mounted to the holding tank 12 such that flow of waste water into the bubbler chamber 14 is substantially independent of the fluid level in the holding tank 12 and the rate of flow of waste water through the holding tank 12. As an example, the bubbler chamber may be a standpipe mounted to the side of a generally rectangular shaped holding tank 12. The bubbler chamber 14 may also include a transparent window or sight glass (not shown) for viewing the contents of the bubbler chamber 14.

The bubbler chamber 14 is coupled to the output of the air pump 16 (FIG. 1) using an air supply conduit 36. With this arrangement air from the air pump 16 is bubbled through the waste water contained within the bubbler chamber 14 and collected in an air space 38 at the top of the bubbler chamber 14. The air space 38 within the bubbler chamber 14 is connected to the sensor 18 (FIG. 1) using a sample conduit 40. In addition, the air space 38 within the bubbler chamber 14 is coupled to an air space 42 located above the waste water fluid level 46 within the holding tank 12 via a return conduit 44 between the air spaces 38 and 42.

Referring back again to FIG. 1, the sample conduit 40 collects gases discharged from the waste water with the bubbled air from the air pump 16 and directs these gases into the sensor 18. The sensor 18 is adapted to detect the concentration of chlorine dioxide within the discharged gases. This concentration of chlorine dioxide gas is an analog of the quantity of chlorine dioxide gas within the waste water. The quantity of chlorine dioxide gas discharged with the bubbled air from the waste water is also a function of the temperature of the waste water. The quantity of chlorine dioxide gas discharged by the bubbler, however, is substantially independent of the depth of waste water through which the air is bubbled and the rate at which the air is bubbled through the waste water.

The sensor 18 may be a standard electrochemical probe that is adapted to sense the concentration of a target chemical gas contained within a stream of gas. As an example the sensor 18 may be a polarographic probe. Such a probe includes an electrolyte, a membrane, and two dissimilar metals. Polarographic probes are well known in the art, and in general perform a quantitative analysis of a gas stream based on measurements of currents and voltages.

Alternately other sensors that are able to detect the concentration of a chemical in a gas stream can be used in place of a polarographic probe. With the arrangement, the gas stream provides a relatively clean background for sensing the target chemical concentration. This is in opposition to the waste water itself, in which, as previously stated, any type of chemical detection may be difficult.

After measurement of the chlorine dioxide concentration, the collected gas stream is directed through the sensor 18 and then through a discharge conduit 48. The discharge conduit 48 is coupled to a gas scrubber 50. The gas scrubber 50 is adapted to remove noxious gases from the gas stream and discharge the remaining harmless gases to the atmosphere. Such a gas scrubber 50 may be a commercially available scrubber that uses various filters and mechanical scrubbers to remove harmful solid and gaseous contaminants from the collected gas stream.

Signals from the sensor 18 are directed over suitable electrical conduits 52 to the processor 22. Similarly signals from the temperature probe 20 are directed over suitable electrical conduits 54 to the processor 22. The processor 22 is adapted to receive and analyze the signals from the polarographic probe in the sensor 18 and the temperature probe 20 mounted in the holding tank 12 in order to determine the concentration of the chlorine dioxide gas present in the waste water. The processor 22 may be a computer or microprocessor adapted to follow preprogrammed instructions and data and to analyze signals from the sensor 18 and temperature probe 20. The processor 22 may also be adapted to receive input and reference data from a user. In addition, the processor 22 may be programmed to monitor predefined levels of the target chemical. This information may then be displayed by the display 24. Hi/low alarms may also be incorporated into the operation of the processor 22 and the display 24. As an example a hi or low alarm could indicate when a predetermined concentration of the target chemical is present.

Moreover, the processor 22 and other controls (not shown), may be used to maintain a target chemical concentration in the waste water. As an example, specific quantities of different chemicals (i.e. disinfectants) may be added to the waste water. Additionally, other liquids (i.e. $H_2O$) may be added to maintain a target chemical concentration in the waste water.

Signals from the processor 22 are directed over suitable electrical conduits 56 to a display 24. The display 24 is adapted to display data from the processor to a user in a visual or recorded format. As such, the display 24 may include LED gauges or graphs that present the analyzed data in a digital or graphical format.

OPERATION

In operation waste water to be monitored is continuously directed through the holding tank 12. During this operation, the stirrer 30 agitates the waste water in the holding tank 12 and directs a changing supply of waste water into the bubbler chamber 14. As the waste water is directed into the bubbler chamber 14 the air pump 16 directs a stream of air bubbles through the waste water contained within the bubbler chamber 14.

This air stream bubbles through the waste water and is collected in the air space 38 at the top of the bubbler chamber 14. As the air stream passes through the waste water, chlorine dioxide gas dissolved within the waste water is released from the solution of waste water and exits from the waste water along with the air bubbles exiting the waste water into the air space 38. The amount of chlorine dioxide gas released from the waste water is in general, a function of the concentration of chlorine dioxide in the waste water and the temperature of the waste water. The discharged gas is thus an analog of the concentration of chlorine dioxide in the waste water.

The gas stream collected in the air space 38 of the bubbler chamber 14 is directed through the sample conduit 40 and into the sensor 18. The polarographic probe within the sensor 18 sends signals to the processor 22 that are indicative of the concentration of the chlorine dioxide gas within the waste water substantially as previously described. These signals, as well as signals from the temperature probe 20, are analyzed using preprogrammed instructions by the processor 22. The resultant data which is indicative of the concentration of the chlorine dioxide in the waste water is then displayed by the display 24.

Thus the method and apparatus of the invention is able to provide an accurate and continuous analysis of the presence and concentration of a target chemical in a solution. Although an illustrative embodiment of the invention is for the detection of chlorine dioxide in waste water, as will be apparent to those skilled in the art, the invention may be adapted to the determination of the presence and concentration of other chemicals contained in other solutions.

While the particular Method and Apparatus for Continuously Measuring the Concentration of Chemicals in Solutions as herein shown and disclosed in detail is fully capable of obtaining the objects and providing the advantages herein before stated, it is to be understood that it is are merely illustrative of the presently preferred embodiments of the invention and that no limitations are intended to the details of construction or design herein shown other than as described in the appended claims.

I claim:

1. A method for monitoring the concentration of a chemical present in a solution comprising:
   agitating a quantity of the solution;
   continuously measuring a temperature of the solution;
   continuously directing a stream of bubbles through a supply of solution received from the quantity of solution to release a quantity of the chemical present in the solution as a dissolved gas;
   collecting gases discharged from the supply of solution;
   measuring the concentration of the chemical present in the discharged gases; and
   determining the concentration of the chemical in the quantity of solution using the measured temperature and concentration of the chemical present in the discharged gases.

2. The method as recited in claim 1 and further comprising:
   agitating the solution in a holding tank and directing the stream of bubbles through the solution received from the holding tank.

3. The method as recited in claim 2 and wherein:
   measuring the concentration of the chemical present in the discharged gas is with a polarographic probe; and
   measuring the temperature of the solution is with a temperature probe.

4. The method as recited in claim 3 and wherein:
   determining the concentration of the chemical in solution is performed with a processor using signals from the polarographic probe and temperature probe.

5. The method as recited in claim 4 and wherein:
   the processor uses preprogrammed instructions.

6. The method as recited in claim 5 and wherein:
   the processor is a microprocessor.

7. The method as recited in claim 4 and wherein:
   directing a stream of bubbles through the solution is with an air pump.

8. The method as recited in claim 4 and further comprising:
   removing noxious gases from the discharged gases; and
   venting the discharged gases to the atmosphere.

9. The method as recited in claim 4 and wherein:
   the processor operates hi/lo indicators that are indicative of a predetermined concentration of the chemical.

10. The method as recited in claim 4 and further comprising:
   displaying the determined concentration of the chemical in solution.
11. The method as recited in claim 4 and wherein:
   the solution is waste water.
12. The method as recited in claim 4 and wherein:
   the chemical is chlorine dioxide in the waste water.
13. An apparatus for continuously monitoring the concentration of a chemical in a solution comprising:
   receiving means for receiving solution;
   agitating means for continuously stirring a quantity of the solution;
   temperature measuring means for continuously measuring the temperature of the solution;
   bubbling means for continuously directing bubbles through a supply of solution received from the quantity of solution in order to release a quantity of the chemical present in the solution as a dissolved gas;
   collecting means for collecting gases discharged from the supply of solution with the bubbles;
   gas measuring means for continuously measuring the concentration of chemical in the collected gases; and
   processing means for receiving signals from the temperature measuring means and gas measuring means and for determining the concentration of the chemical based on the temperature of the solution and the concentration of the chemical in the collected gases.
14. The apparatus as recited in claim 13 and wherein:
   the receiving means is a holding tank.
15. The apparatus as recited in claim 14 and wherein:
   the means for directing bubbles through the solution is an air pump.
16. The apparatus as recited in claim 15 and wherein:
   the means for measuring the concentration of the chemical in the collected gases is a polarographic probe; and
   the means for measuring the temperature of the solution is a temperature probe.
17. The apparatus as recited in claim 16 and wherein:
   the processing means is a microprocessor having preprogrammed instructions.
18. The apparatus as recited in claim 17 and further comprising:
   display means for displaying signals from the processing means.
19. The apparatus as recited in claim 18 and further comprising:
   gas scrubbing means coupled to the collected gases for removing noxious gases and discharging the collected gases to the atmosphere.
20. A system for determining the concentration of a chemical in a solution, comprising:
   a holding tank for receiving the solution;
   at least one agitator positionable in the holding tank for continuously stirring the solution in the holding tank;
   a temperature probe mounted within the holding tank for continuously measuring the temperature of the solution and for continuously generating signals in response to the measured temperature;
   an air pump arranged for continuously directing air bubbles through solution received from the holding tank and for continuously releasing a quantity of the chemical present in the solution as a dissolved gas;
   a bubbler chamber mounted to the holding tank and arranged for continuously collecting gases discharged from the received solution received from the holding tank;
   a sensor in fluid communication with the bubbler chamber adapted for measuring the concentration of the chemical in the gases collected and for generating signals in response to the measured concentration; and
   a processor adapted for receiving signals from the temperature probe and sensor and for determining the concentration of the chemical in the solution based on the temperature of the solution and the concentration of the chemical in the gases collected in the bubbler chamber.
21. The system as recited in claim 20 and further comprising:
   display means for displaying the concentration of the chemical in the solution.
22. The system as recited in claim 20 and wherein:
   the sensor is a polarographic probe.
23. The system as recited in claim 20 and wherein:
   the solution is waste water.
24. The system as recited in claim 23 and wherein:
   the chemical is chlorine dioxide.
25. The system as recited in claim 20 and further comprising:
   gas scrubber means connected to the bubbler chamber for removing noxious gases from the gases collected in the bubbler chamber.
26. The system as recited in claim 20 and wherein:
   the display means includes hi-low alarms for indicating a predetermined concentration of the chemical in the solution.

* * * * *